United States Patent [19]

Schegk

[11] Patent Number: 5,272,738
[45] Date of Patent: Dec. 21, 1993

[54] DEVICE FOR MONITORING THE ATMOSPHERE WITHING A NUCLEAR REACTOR CONTAINMENT

[75] Inventor: Claus-Detlef Schegk, Klingnau, Switzerland

[73] Assignee: Asea Brown Boveri Ltd., Baden, Switzerland

[21] Appl. No.: 937,759

[22] Filed: Sep. 1, 1992

[30] Foreign Application Priority Data

Sep. 30, 1991 [CH] Switzerland ............... 2886/91

[51] Int. Cl.⁵ ............................. G21C 19/42
[52] U.S. Cl. ........................ 376/314; 376/310; 376/308
[58] Field of Search ............... 376/293, 310, 277, 308, 376/314, 245; 976/DIG. 167

[56] References Cited

U.S. PATENT DOCUMENTS

| 3,667,370 | 6/1972 | Noble | 376/293 |
| 4,520,654 | 6/1985 | Terhune | 73/24 |
| 4,863,677 | 9/1989 | Eckardt | 376/313 |
| 5,091,144 | 2/1992 | Dillmann et al. | 376/283 |

FOREIGN PATENT DOCUMENTS

| 52-64591 | 5/1977 | Japan . |
| 54-135595 | 10/1979 | Japan . |
| 59-104584 | 6/1984 | Japan . |
| 1-276087 | 11/1989 | Japan . |

*Primary Examiner*—Donald P. Walsh
*Assistant Examiner*—Meena Cheliah
*Attorney, Agent, or Firm*—Burns, Doane, Swecker & Mathis

[57] ABSTRACT

In a device for monitoring the atmosphere within the containment shell (1) of a reactor plant, a sample removal means (41) is provided in the containment shell, from which a gas mixture is led via a measuring line (42) through a measuring zone (14) and subsequently discarded. The concentration of the gas is reduced upstream of the measuring zone (14) in a dilution plant (40).

9 Claims, 1 Drawing Sheet

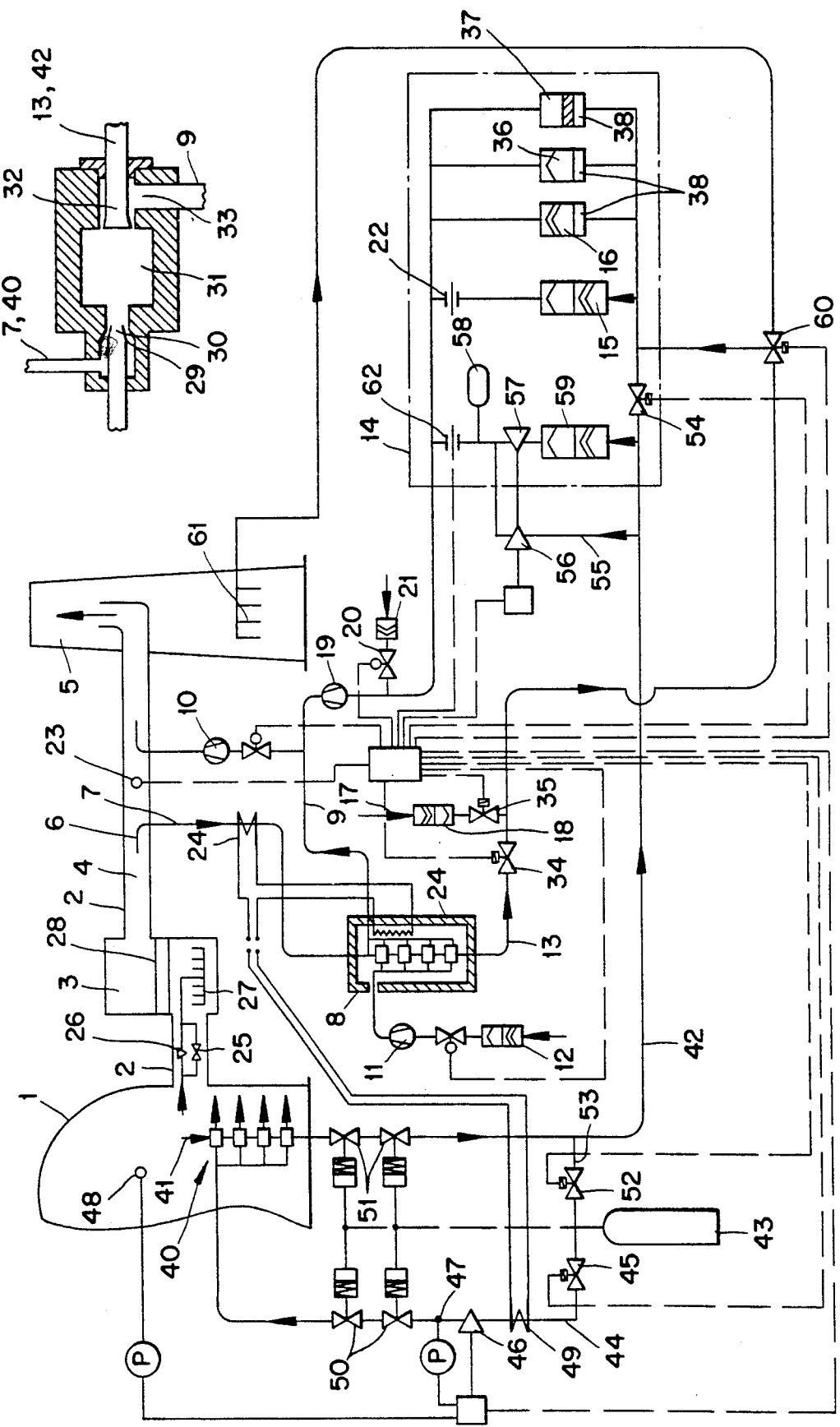

DEVICE FOR MONITORING THE ATMOSPHERE WITHING A NUCLEAR REACTOR CONTAINMENT

BACKGROUND OF THE INVENTION

1. Field of the Invention

The invention relates to a device for monitoring the atmosphere within the containment shell of a reactor plant, a sample removal means being provided in the containment shell, from which a gas mixture is led via a measuring line through a measuring zone and subsequently discarded.

DISCUSSION OF BACKGROUND

The atmosphere in the containment shell of a nuclear power plant consists as a rule of air, steam, hydrogen, $CO_2$, noble gases, iodine and aerosols. In normal plant operation this mixture, having an activity of approx. $10^3$ Bq/m$^3$, is led from the containment shell via a ventilation system directly into the stack. In the event of an accident with a small leakage in the primary system, in which the activity is between $10^3$ Bq/m$^3$ and $10^8$ Bq/m$^3$, the gas is also led off via the ventilation system directly into the stack. In the event of a major accident with, for example, core meltdown, the activity can become greater than $10^{14}$ Bq/m$^3$. The ventilation system is shut off in the event of the major accident, with the result that the pressure in the containment shell increases. In order to avoid too high a pressure increase, the containment shell is relieved via a filter system. In this filter system (e.g. dry filters, wet filters) the activity of iodine and aerosols is reduced by at least a factor of 1000. Downstream of the filter system the activity of the gas is then determined in a measuring zone.

The measuring equipment used for normal operation, such as balancing filters and aerosol cannot be used in the event of an accident because of the residual very high activity in the subsequent clean gas line, which leads to the stack, since the measuring range would be exceeded and handling of the balancing filter would not be guaranteed. Therefore, special instruments having a high measuring range and complex shielding, as well as complicated devices for handling the balancing filter are normally used.

In the event of an accident, it is therefore useful also to monitor the atmosphere inside the containment shell, as long as the pressure relief is not yet in operation, in order to obtain a measure of the increasing activity, and the activity that can be expected. In this case, the activity of the sample gas is also too high for the evaluation instruments that are used in normal operation.

SUMMARY OF THE INVENTION

Accordingly, one object of the invention is to avoid these disadvantages. Its object is, with a plant of the aforementioned type, to operate the plant using the existing measuring instruments and equipment even in the event of an accident.

According to the invention this is achieved by reducing the activity concentration of the gas upstream of the measuring zone in a dilution plant.

The advantages of the invention can be seen, inter alia, in the elimination of the heavy shielding of the entire measuring zone, which has hitherto been conventional. The shielding for transport of the balancing filter, which has to be measured, is also eliminated, greatly reducing the hazard to the operating personnel.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 shows a simplified circuit diagram of an exhaust air-side part of a reactor plant;

FIG. 2 shows the schematic diagram of a dilution stage.

Only the elements essential to the understanding of the invention are shown. The whole primary and secondary parts, for example, of the reactor plant are not shown. The direction of flow of the working fluid is shown by arrows.

DESCRIPTION OF THE PREFERRED EMBODIMENTS

Referring now to the drawings, wherein like reference numerals designate identical or corresponding parts throughout the several views, in FIG. 1 the containment shell of the reactor is designated with 1. A pressure relief line 2, called crude gas line below in its first part, leads from the containment shell to the filter system 3. A control valve 25 and a bursting disk 26 are disposed in two parallel trains in the crude gas line for defined pressure relief. Throughput measurement, not shown here, also takes place in the crude gas line. The present filter system operates according to the wet filter principle, but this is, of course, not necessary. The water is atomised in venturi fittings 27, thus cleaning the gases. The cleaned gases then pass through a water separator 28. They then enter a second part of the pressure relief line 2, designated as clean gas line 4 below, which leads to the stack 5.

Sample removal means 6 are disposed in the clean gas line 4, from which a gas sample is continuously removed and led into a removal line 7. As an example, with a total exhaust gas rate of 20,000 m$^3$/h, approximately 10 m$^3$/h is tapped off. This gas sample is heated by either an electrical heater 24, or one operated by heat exchange, over preferably the whole length of the removal line 7, in order to avoid condensation.

From the removal line, a part stream is fed to the dilution plant 8. This multi-stage plant operates with a specific volume flow rate of particle-free compressed air. This is prepared in a compressor 11, having an iodine filter and an aerosol filter 12 connected upstream. Of the several dilution stages, in principle only the first two stages are heated, since even with pure steam in the clean gas line 4, it is no longer possible to fall below the dew point temperature after the second stage.

Downstream of the dilution plant 8, which is described below, the sample flow is led via the measuring line 13 into the actual measuring zone 14, which is also intended for normal operation of plant. Upstream of the measuring zone 14, the measuring line 13 is combined via a three-way valve 60 with a measuring line used for normal operation. The latter carries the exhaust gases that are to be continuously measured, which are removed by means of a sample removal manifold 61 from the stack 5.

The measuring zone 14, shown highly simplified, comprises, on the one hand, a combination 15 of aerosol and iodine balancing filters for discontinuous measurement. An aerosol monitor 16, an iodine monitor 36 and a noble gas monitor 37 are provided for quasicontinuous monitoring. These three monitors are each equipped with a radiation detector 38. The relative activity of the aerosols is detected using this simple display. It also determines the replacement intervals for the balancing filters.

In normal operation usually a discontinuous measurement is made via the elements 15 once per week. In the event of an accident, by contrast, it is provided for a measurement to be made every four hours. The balancing filters are removed for this, taken into a separate room and there analysed for specific nuclides using a spectrometer.

Before the measurement, the measuring zone 14 is flushed, so that the filter activity caused by the noble gas components is reduced to an insignificant level and the actual measurement is not falsified. For this the measuring line 13 is closed by means of a shut-off element 34 and the flush-air line 17 is opened by means of a shut-off element 35. Atmospheric air is taken in by the delivery pump 19 and passes via iodine and aerosol filters 18 into the measuring zone. The flush-air is exhausted into the return line 9. It can, of course, also be led off directly into the stack 5.

When the measurement itself is to be made, the flush-air line 17 is closed with the shut-off element 35 and the measuring line 13 is opened with the shut-off element 34. The mixture that is to be measured is taken in via the same delivery pump 19. Since this pump is designed for the higher rate of flush air, atmospheric air is also taken in in the case of the measurement for control purposes. For this purpose, a control valve 20 with upstream aerosol filter 21 is located upstream of the pump in a branch line. Upstream of the junction of the part of the measuring zone having the aerosol monitor with the part having the balancing filters, a flow meter 22 is disposed in the latter. The flow rate across the aerosol and iodine filters is measured there and integrated over the dust collection time. The activity concentration values are determined in this manner. The concentration is correlated with the throughput measurement in order to derive the activity output rate.

Although, as mentioned above, the throughput is also measured in the crude gas line, a correlation with this measurement would lead to incorrect results, since with pressure relief the throughputs in the crude gas line and in the clean gas line can be very different, especially in the starting phase. This may be caused, for example, by condensation of the vapour part in the still cold water reservoir of the filter system 3. Consequently the flow rate is determined a further time at 23 in the clean gas line 4. This can be a venturi measurement or a determination via a pressure/temperature measurement. The result is combined with the concentration values in order to determine the activity output rates.

The following plant parts are used to determine the activity concentration within the containment shell 1, which precedes the above described measurement: a multi-stage dilution plant 40 is disposed in the containment shell. Sample removal is indicated with the arrow 41. The processed gas sample is introduced into a measuring line 42, leading to the measuring instrument 14. The dilution gas, here compressed air or nitrogen, is prepared in a pressure bottle 43 located outside the containment shell and introduced via a feed line 44 into the dilution plant.

In addition to a shut-off element 45, a pressure reduction valve 46 is located in this feed line 44. Since in the event of an accident, pressures between 1 and 7 bar could occur in the containment shell, the pressure of the dilution gas in the feed line must be correspondingly adapted. Therefore the pressures measured in the feed line at 47 and in the containment shell at 48 are applied to the regulating unit of the pressure reduction valve.

The feed line 44 is provided with a heater 49, in order to heat the dilution air at least approximately to the temperature prevailing in the containment shell 1.

Furthermore, regulating elements 50, 51 are provided in the feed line 44 and in the measuring line 42. They are generally located in the empty space between the containment shell and the outer concrete shell, which is not shown. They are designed according to safety class 2 and exist as a dual system. At the beginning of the measurement, care should be taken that the regulating elements 50 in the feed line 44 are opened before the regulating elements 51 in the measuring line 42; after completion of the measuring operation, care should be taken that the regulating elements in the feed line are closed before those in the measuring line. This measure prevents gas mixture with too high an activity passing via the dilution plant 40 into the measuring line 42 and from there into the open.

A dilution stage shown in FIG. 2, which is relevant to both the dilution plant 8 as well as the dilution plant 40, functions as follows: the compressed air provided flows through an annular gap 29 around the intake nozzle 30 for the gas mixture that is to be diluted. Because of the underpressure thus occurring, the aerosol is sucked in at a certain volume flow rate and homogeneously mixed with the clean air in the mixing chamber 31. If the volume flow rate of the clean air is increased, the flow rate in the annular gap increases to the same degree. The underpressure at the suction nozzle thus increases, causing an increase of the volume flow rate of the gas mixture. Both volume flow rates are thus coupled via the underpressure and their ratio also remains constant for different initial pressures.

A dilution of $1:10^4$ is sought in the dilution plant 8, whilst in the dilution plant 40 a dilution of $1:10^{6-7}$ is carried out. It is advantageous here to carry out the dilution in several cascades, reducing the demand for clean dilution air. Only a part of the diluted sample, which was taken from the removal line 7 or the sample removal means 41 in the containment shell 1 respectively, is taken from the mixing chamber 31 and fed to the respective next stage. This part stream removal is carried out via the suction nozzle 32. Care must be taken here that this removal is carried out under isokinetic conditions. These exist when the flow rate in the nozzle 32 at the point of suction is the same as that in the flow channel. Different suction volume flow rates can be adapted by means of different nozzle diameters to different overall volume flow rates. This is important the last stage. As an example it may be assumed that, from the overall flow rate, only 0.3 m³/h is used for further dilution. After dilution, a total of approx. 3 m³/h is thus fed to the measuring equipment. The residual air of 16.2 m³/h for all 6 dilution stages shown in the case of the example (only 4 stages in each case are shown in FIG. 1), which remains after isokinetic removal of the part stream, in the dilution plant 8, flows through the exhaust connection 33 out into the return line 9 (FIG. 1). The rest of the sample air and the air from the exhaust connection 33 are transported in this return line by a pump 10 back into the clean gas line 4. Care should be taken with this return that there is no counterpressure in the mixing chamber of the dilution stage, which could affect the dilution ratio. In the dilution plant 40 the residual air is exhausted back into the containment shell 1, as indicated by the arrows.

The activity of the materials that are separated out is reduced by the dilution to a level that is usual for normal operation also. The handling and evaluation of the measuring equipment can thus be carried out conventionally even in the event of an accident.

The measuring line 13, in the dilution plant 8, and the measuring line 42 in the dilution plant 40 (FIG. 1), which lead to the actual measuring zone 14, are connected to the suction nozzle 32 of the last stage.

In order to be able to measure both the stack air and the atmosphere within the containment shell 1 independently of each other in the event of an accident, the measuring zone 14 is equipped with an additional balancing filter 59 and a flow meter 62.

The aerosol and iodine balancing filter 59 is equipped with a by-pass line 55 provided for start up. The measurement values of the flow meter 62 and, where applicable, those of the temperature and pressure measuring sensors (which are located in the same pipe train as the flow meter), not illustrated, are used as regulating variables for the coupled control elements 56, 57 in the by-pass line 55 and behind the balancing filter 59. For start up the sample removal system is operated for several minutes with by-pass line 55 open. This guarantees that the whole system is flushed with representative sample air. After the start-up process, in which the removal volume flow rate was adjusted, a switchover is executed from the by-pass line 55 to the line to the balancing filter 59. The regulating elements 50 and 51 are open during all these processes.

In the event of an accident the sample removal means is put into operation discontinuously as required. For the measurement itself, the flush line 53 is closed using the valve 52. After the volume control has been carried out, the diluted gas sample is led through the aerosol and iodine filter. As in the method discussed above, the flow rate is measured and integrated over the dust collection time. Gas flow rates of between 1 and 3 m³/h are measured. The dust collection time can be between one and several minutes. The filter 59 covered with dust after the measurement can be evaluated in the laboratory using the detectors used for filter evaluation in normal operation, e.g. germanium detectors.

An additional measuring point is provided downstream of the balancing filters, in order to determine the proportion of noble gases in the sample. This may be a gas bottle or a so-called "gas mouse" 58.

After the measurement the measuring zone 14 is flushed. To this end the pressure medium, which is present anyway, is drawn from the bottle 43. The elements 45 and 51 in the feed line and the measuring line are closed. With the reduction valve 52 open, the dilution gas is transported via the flush line 53 into the measuring line 42 and from there through the measuring zone 14. Since only the balancing filters 59 are required for the measurement, the line leading to the monitors 3638 can also be closed for flushing and measuring purposes using the shut-off element 54. The flush medium is exhausted into the return line 9. It can, of course, also be exhausted directly into the stack 5. Naturally, the measuring zone could also be flushed in this case with the above described flushing media 17-19 and by the process described there.

Obviously numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A device for monitoring an atmosphere within a containment shell of a nuclear reactor plant, comprising:
    sample removal means provided in the containment shell;
    a measuring line connected to the sample removal means for leading a gas sample from the containment shell;
    a measuring zone located in the measuring line and disposed outside of the containment shell through which the sample is led for measuring the activity of the gas sample;
    a dilution plant located in the measuring line and disposed in the containment shell for reducing the activity concentration of the gas sample upstream of the measuring zone;
    the dilution plant being adapted to be connected to a clean, pressure-controlled dilution gas source located outside the containment shell.

2. The device as claimed in claim 1, wherein the dilution gas is heated by means of a heater before introduction into the dilution plant.

3. The device as claimed in claim 1, wherein the dilution plant is provided with a plurality of stages for dilution of the gas sample.

4. An apparatus for monitoring gases within a containment of a nuclear reactor plant, comprising:
    sampling means for drawing a sample of gas within the atmosphere in the containment;
    a dilution plant connected to the sampling means for diluting the gas sample with clean dilution gas, the dilution plant being adapted for connection with a source of clean, pressurized dilution gas;
    a measuring line connected to the dilution plant for removing the diluted gas sample from the containment; and,
    a measuring zone connected to the measuring line outside of the containment for measuring the activity of the diluted gas sample.

5. The apparatus as claimed in claim 4, further comprising a heater to heat the dilution gas before introduction to the dilution plant.

6. The apparatus as claimed in claim 4 wherein the dilution plant comprises a plurality of dilution stages connected in series for diluting the sample gas in steps.

7. A method for monitoring gases within a containment shell of a nuclear reactor plant, comprising the steps of:
    sampling gases in a containment shell;
    diluting the gas sample in a dilution plant with clean, pressurized dilution gas;
    removing the diluted gas sample from the containment shell;
    directing the diluted gas sample through a measuring zone; and,
    measuring selected activity of the diluted gas sample.

8. The method as claimed in claim 7, further comprising the step of heating the dilution gas before diluting the gas sample.

9. The method as claimed in claim 7, wherein the step of diluting the gas sample is performed is several stages.

* * * * *